US 7,478,565 B2

(12) United States Patent
Young (10) Patent No.: US 7,478,565 B2
(45) Date of Patent: Jan. 20, 2009

(54) METHOD & APPARATUS FOR FLUID FLOW RATE AND DENSITY MEASUREMENT

(76) Inventor: Alan M. Young, 21600 Summit Rd., Los Gatos, CA (US) 95033

( * ) Notice: Subject to any disclaimer, the term of this patent is extended or adjusted under 35 U.S.C. 154(b) by 0 days.

(21) Appl. No.: 12/017,992

(22) Filed: Jan. 22, 2008

(65) Prior Publication Data

US 2008/0173085 A1 Jul. 24, 2008

Related U.S. Application Data

(60) Provisional application No. 60/881,698, filed on Jan. 23, 2007.

(51) Int. Cl.
*G01F 1/46* (2006.01)
(52) U.S. Cl. .................................. 73/861.65
(58) Field of Classification Search ............. 73/861.66, 73/861.65, 861.42, 861.47, 861.52
See application file for complete search history.

(56) References Cited

U.S. PATENT DOCUMENTS

| 5,379,650 | A | * | 1/1995 | Kofoed et al. ............ 73/861.52 |
| 6,164,141 | A | * | 12/2000 | Chalvignac et al. ...... 73/861.52 |
| 6,314,821 | B1 | * | 11/2001 | Allan ...................... 73/861.52 |
| 6,865,957 | B1 | | 3/2005 | Hughes et al. |

* cited by examiner

*Primary Examiner*—Jewel Thompson
(74) *Attorney, Agent, or Firm*—Vierra Magen Marcus & DeNiro LLP (57) ABSTRACT

A fluid flow rate and density measuring apparatus is disclosed including a section of cylindrical conduit comprising a measurement section or housing for the flow sensor. The flow sensor housing is fixedly attached to a conduit at its distal ends allowing fluid to pass through the open ends of the sensor housing as fluid flows through the conduit. An elongated, streamlined, cylindrically symmetric structure is located within the housing with its longitudinal axis aligned along that of the housing thereby forcing fluid through the annular gap between the exterior of the elongated cylindrical structure and the interior wall of the sensor housing.

37 Claims, 7 Drawing Sheets

Schematic representation of sensor with dynamic pressure ports 30 and 40 (for $P_1$ and $P_2$) incorporated into a removable subassembly 41.

Figure 1. Schematic representation of sensor with dynamic pressure ports 30 and 40 (for $P_1$ and $P_2$) incorporated into a removable subassembly 41.

Figure 2. Schematic diagram representing the measurement method to determine mass flow rate, volumetric flow rate and density Figure 3. Schematic representation of sensor with pressure ports for dynamic pressures $P_1$ and $P_2$ incorporated into sensor support.

Figure 4. Schemtic representation of sensor with pressure ports for dynamic pressure $P_1$ and static pressure $P_0$ incorporated into a removable subassembly.

Figure 5. Schematic diagram representing the measurement method for the apparatus depicted in figure 4 to determine mass flow rate, volumetric flow rate and density Figure 6. Flow rate test data from sensor with 0.36-inch O.D. cylindrical structure within a housing of 0.5-inch I.D. exhibiting a flow rate measurement range of nearly 50:1 independent of fluid flow regime.

Figure 7. Sensor test results on water demonstrating substantial sensor immunity to piping configuration and flow velocity profile nonuniformities.

METHOD & APPARATUS FOR FLUID FLOW RATE AND DENSITY MEASUREMENT

CROSS REFERENCE TO RELATED APPLICATION

The present application claims priority under 35 U.S.C. §119(e) to U.S. Provisional Patent Application No. 60/881,698 to A. Young, filed Jan. 23, 2007, entitled "Method & Apparatus For Fluid Flow Rate And Density Measurement," which application is incorporated by reference herein in its entirety.

BACKGROUND OF THE INVENTION

Devices are known for measuring fluid flow using both static and dynamic pressure measurements. Dynamic pressure is the component of fluid pressure that represents fluid kinetic energy (i.e., is responsive to fluid motion), while static pressure represents only hydrostatic effects. Dynamic pressure results from the force of a fluid impinging on a surface whereas hydrostatic pressure measures only static pressure. Hydrostatic pressure exists regardless of whether the fluid is flowing, whereas dynamic pressure exists only when fluid is flowing. Traditional differential pressure ("DP") devices measure the hydrostatic pressure drop across a structure inserted into the flow stream specifically designed to produce a substantial pressure drop (e.g., an orifice plate) in order to measure flow rate. Hydrostatic pressure differentials measured are smaller than dynamic pressure signals resulting in very limited dynamic flow measurement range.

U.S. Pat. No. 6,865,957 ("the '957 patent"). The '957 patent teaches a mass flow measurement by subtracting two dynamic pressure measurements. With reference to FIG. 4 of the '957 patent, a first dynamic pressure measurement $P_1$ is obtained at the apex of a conically-shaped end-piece; a second dynamic pressure measurement $P_2$ is obtained at a different location (i.e., different radial location) from a pressure port located within the "cylindrical portion" of the body. According to the '957 patent, solely the difference between these two dynamic pressure signals determines fluid mass flow rate. For example, the '957 patent states at column 4, lines 29-31, "FIG. 5 is a schematic flow diagram depicting the process employed in determining mass flow with the device of the present invention" and FIG. 5 explicitly illustrates that $P_1-P_2$ determines mass flow. At col. 6, lines 51-54, "The difference between pressures $P_1$ and $P_2$ are then determined either manually or automatically and, through the use of tables or graphs determine the mass flow of fluid through device 10."

SUMMARY OF THE INVENTION

In accordance with the present invention, a fluid flow rate and density measuring apparatus includes a section of cylindrical conduit comprising a measurement section or housing for the flow sensor. The flow sensor housing is fixedly attached to a conduit at its distal ends allowing fluid to pass through the open ends of the sensor housing as fluid flows through the conduit. An elongated, streamlined, cylindrically symmetric structure is located within the housing with its longitudinal axis aligned along that of the housing thereby forcing fluid through the annular gap between the exterior of the elongated cylindrical structure and the interior wall of the sensor housing. The elongated cylindrical structure is fixedly attached within the sensor housing by one or more supports. The elongated cylindrical structure is dimensioned appropriately to accommodate the interior dimensions of the housing and the particular nature of the fluids, flow rates and densities to be measured. The present invention can also be used to measure bi-directional air flows for purposes of pulmonary testing in which case the flow sensor is not attached to a conduit.

In addition to the above mentioned elements, the present invention also includes at least one dynamic pressure measurement, which may be obtained at a location anywhere along the length of the annular region between the elongated cylindrical structure and the interior wall of the cylindrical sensor housing. In a preferred embodiment, a first dynamic pressure measurement is obtained from an upstream-facing pressure port and a second dynamic pressure measurement is obtained from an adjacent, but oppositely directed (i.e., downstream-facing) pressure port. Thus, two dynamic pressure signals may be obtained allowing their combination to simultaneously determine the fluid mass flow rate, volumetric flow rate and density of the fluid (if it is a gas) passing through the apparatus.

In another embodiment, a dynamic pressure measurement is obtained from an upstream-facing pressure port (or equivalently from a downstream-facing pressure port) within the annular space between the elongated cylindrical structure and the interior wall of the sensor housing. A second pressure measurement is obtained at the interior wall of the sensor housing to obtain a static pressure measurement. Combining the two pressure signals allows simultaneous determination of fluid mass flow rate, volumetric flow rate and density passing through the flow sensor.

In yet another embodiment, the mass flow measurement method of the present invention can be applied to the devices described in U.S. Pat. No. 6,865,957 B1 to provide for an improved mass flow rate measurement independent fluid of density and, in addition, provide simultaneous determination of volumetric flow rate and gas density.

DETAILED DESCRIPTION

Figure 1:
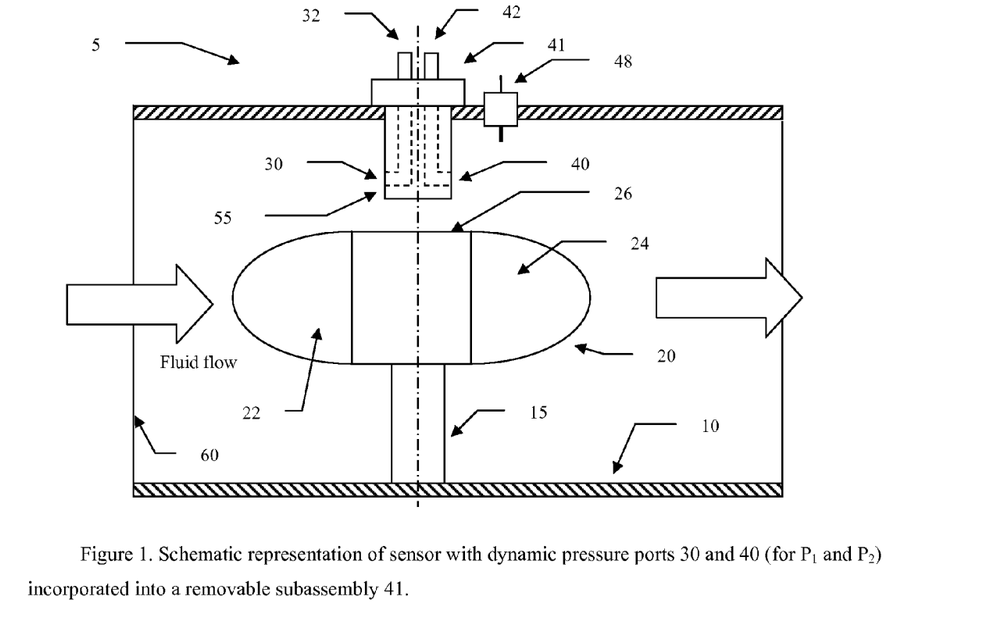
FIG. 1. Schematic representation of sensor with dynamic pressure ports for $P_1$ and $P_2$ incorporated into a removable subassembly.

With reference to FIG. 1, a fluid flow rate and density measuring sensor 5 includes a tubular piece of conduit 10 comprising a measurement section or housing for the flow sensor. For industrial fluid flow measurement applications, the flow sensor housing is connected to a conduit allowing fluid to pass through the sensor. For pulmonary testing applications, a suitable mouthpiece connected to the sensor entrance would allow a patient to inhale/exhale air through the sensor. An elongated cylindrical structure 20 with streamline-shaped ends 22 and 24 is located within the housing with its longitudinal axis aligned along that of the housing thereby forcing fluid to flow through the annular region between the exterior of the elongated cylindrical structure and the interior wall of the sensor housing. The streamlined cylindrical structure 20 may not necessarily have a straight cylindrical segment 26 interposed respectively between the two ends 22 and 24. Additionally, the elongated cylindrical structure need not exhibit bilateral symmetry about its mid-point (e.g., the structure may be shaped differently at one distal end compared to the other and/or exhibit a variable cross-sectional shape along its length). The elongated cylindrical structure should preferably have a streamlined shape to minimize its drag coefficient to reduce the corresponding fluid pressure drop across its length.

The gap between the entire length of streamlined cylindrical structure 20 and the inner wall of the sensor housing is generally referred to herein as the "annular region". Additionally, ends 22 and 24 may or may not have the same shape. The elongated cylindrical structure 20 is fixedly attached within the sensor housing by support 15 (but may include a plurality of supports to insure alignment and centering of the elongated structure along the longitudinal axis of the housing and conduit). The elongated cylindrical structure 20 is dimensioned appropriately to accommodate the interior dimensions of the housing and the particular nature of the fluids, flow rates and densities to be measured.

Two pressure measurements are obtained in the annular region between the elongated cylindrical structure and the interior wall of the cylindrical sensor housing.

A first dynamic pressure measurement $P_1$ is obtained from an upstream-facing pressure port 30 and a second dynamic pressure measurement $P_2$ is obtained from an adjacent, but oppositely directed (i.e., downstream-facing) pressure port 40. Thus, two dynamic pressure signals so obtained allow their combination to simultaneously determine fluid mass flow rate $Q_M$, volumetric flow rate $Q_V$ and density of the fluid $\rho$ (if it is a gas) passing through the apparatus. Fluid temperature is monitored by temperature sensor 48. Additionally, dynamic pressure ports for $P_1$ and $P_2$ can be incorporated into subassembly 41 allowing for straightforward assembly, removal and replacement of the subassembly if desired. To simplify design, the temperature and pressure sensors may be combined into one removable subassembly or module. The following relationships and definitions apply to the present invention:

$P_0$=static pressure near the location of the dynamic pressure ports (1)

$P_1$=fluid dynamic pressure facing up-stream (2)

$P_2$=fluid dynamic pressure facing down-stream (3)

$V_C$=average fluid velocity in conduit (4)

$A_C$=conduit cross-sectional area (5)

$Q_V$=fluid volumetric flow rate=$V_C A_C$ (6)

$Q_M$=fluid mass flow rate=$\rho Q_V=\rho V_C A_C$ (7)

If the fluid flowing through the sensor is a liquid, $\rho_L$=liquid density=$\rho_L(T)$ (8)

Where $\rho_L(T)$ is the liquid density as a function of absolute fluid temperature T. If the fluid is a gas, the density of the gas, $\rho_G$, can be expressed as $\rho_G=n/v=P_0/(RTZ)$ (9)

with gas density $\rho_G$ varying according to the General Gas Law as represented by (10) through (14) below.

$Pv=nRTZ$ (10)

where n is proportional to mass of the gas contained in volume v v=volume occupied by gas (11)

R=Universal Gas Constant (12)

T=absolute temperature of gas (13)

Z=a gas compressibility factor (Z=1 for ideal gases) (14)

As fluid flows through a conduit of cross-sectional area $A_C$ with average velocity $V_C$, the cylindrical structure directs flow into the annular region of area A with average velocity, V, given by $V=V_C(A_C/A)$ (15a)

since $AV=A_C V_C$ (neglecting fluid compressibility). When fluid is flowing, the upstream dynamic pressure $P_1$ measured at 30 is expressed as $P_1=\frac{1}{2}\rho V^2+P_0$ (16)

The downstream-facing dynamic pressure $P_2$ measured at 40 is expressed as $P_2=-\frac{1}{2}\rho V^2+P_0$ (17)

where $P_0$ is the static pressure of the fluid at the location where the two dynamic pressures are measured. Note that if $P_2$ is subtracted from $P_1$ one obtains $P_1-P_2=\rho V^2$ (18)

If $P_1$ is added to $P_2$ one obtains $P_1+P_2=2P_0=2ZRT\rho$ (gases) (19)

$P_1+P_2=2P_0$ (liquids) (20)

For gases, if (18) is divided by (19) one obtains $(P_1-P_2)/(P_1+P_2)=V^2/2ZRT$ (gases) (21)

The average fluid velocity V is obtained from (21) yielding $V=\{2ZRT(P_1-P_2)/(P_1+P_2)\}^{1/2}$ (gases) (22)

For gases, the volumetric flow rate $Q_{VG}$ can be expressed from (6) above as $Q_{VG}=AV=A\{2ZRT(P_1-P_2)/(P_1+P_2)\}^{1/2}$ (24)

Using (7) above, the associated gas mass flow rate $Q_{MG}$ is given by $Q_{MG}=\rho_G AV=A\{(P_1-P_2)(P_1+P_2)/2ZRT\}^{1/2}$ (25)

Gas density $\rho_G$ can be expressed as $\rho_G=(P_1+P_2)/(2ZRT)$ (26)

Thus for gases, mass flow rate $Q_{MG}$, volumetric flow rate $Q_{VG}$ and density $\rho_G$ can be determined concurrently by combining a fluid temperature measurement, T, with two dynamic pressure readings $P_1$ and $P_2$ as expressed above in equations (24) through (26). Because mass flow rate $Q_{MG}$, volumetric flow rate $Q_{VG}$ and density $\rho_G$ are determined simultaneously from the same pressure sensing means positioned at substantially the same physical location, their measured values are self-consistent in contrast to measuring gas density using a separate pressure sensor or transducer located elsewhere in the sensor or the attached conduit.

Likewise for liquids, $$P_1-P_2=\rho_L V^2 \quad (27)$$

The average liquid velocity, V, can be expressed as, $$V=\{(P_1-P_2)/\rho_L(T)\}^{1/2} \quad (28)$$

Thus the liquid volumetric flow rate, $Q_{VL}$, is given by $$Q_{VL}=AV=A\{(P_1-P_2)/\rho_L(T)\}^{1/2} \quad (29)$$

The corresponding liquid mass flow rate, $Q_{ML}$, is expressed as $$Q_{ML}=\rho_L AV=A\{(P_1-P_2)\rho_L(T)\}^{1/2} \quad (30)$$

Where $\rho_L(T)$ represents the liquid density as a function of fluid temperature T as expressed by $$\rho_L(T)=\rho_L(T_R)[1+\alpha(T,T_R)] \quad (31)$$

where $\alpha=\alpha(T,T_R)$ represents a general functional relationship of liquid density versus temperature T relative to that at reference temperature, $T_R$, and $\rho_L(T_R)$ is the known liquid density at a reference temperature $T_R$; at $T=T_R$, $\alpha(T,T_R)=0$.

Figure 2:
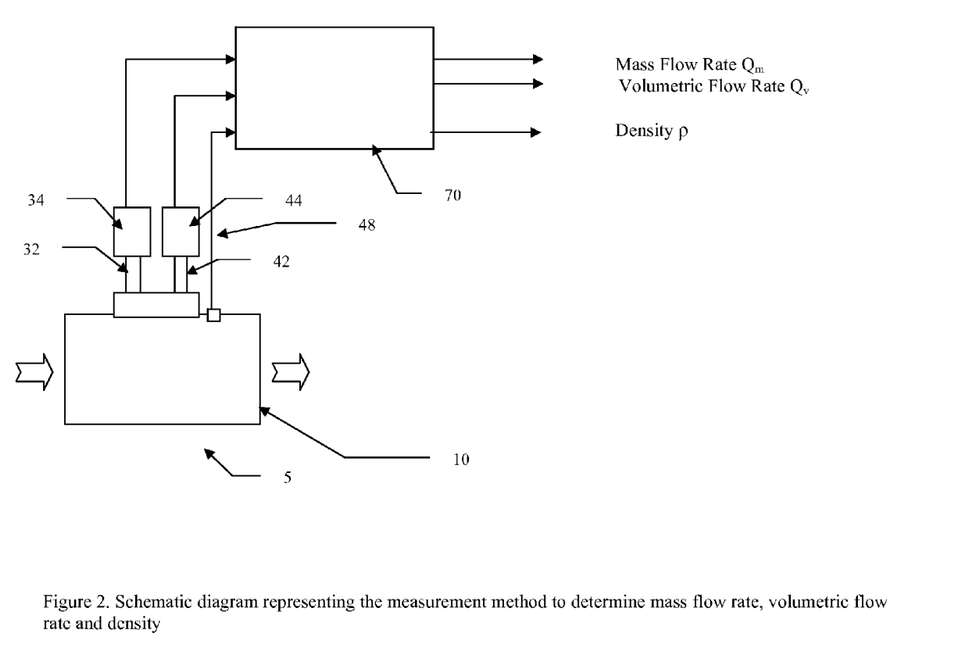
FIG. 2. Schematic diagram illustrating the measurement method to determine fluid mass flow rate, volumetric flow rate and density.

With reference to FIG. 2, external pressure ports 32 and 42 respectively communicate the upstream and downstream dynamic fluid pressures to pressure sensing means 34 and 44. Electronic output signals from pressure sensing means 34 and 44 representative of dynamic pressures $P_1$ and $P_2$ are input to processing means 70 together with fluid temperature, T, sensed by temperature sensor 48. The outputs of processing means 70 provide electronic output signals and output indications representative of fluid mass flow rate, fluid volumetric flow rate and fluid density in accordance with equations (24), (25) and (26) when measuring gases and in accordance with equations (29), (30) and (31) when measuring liquids.

Figure 3:
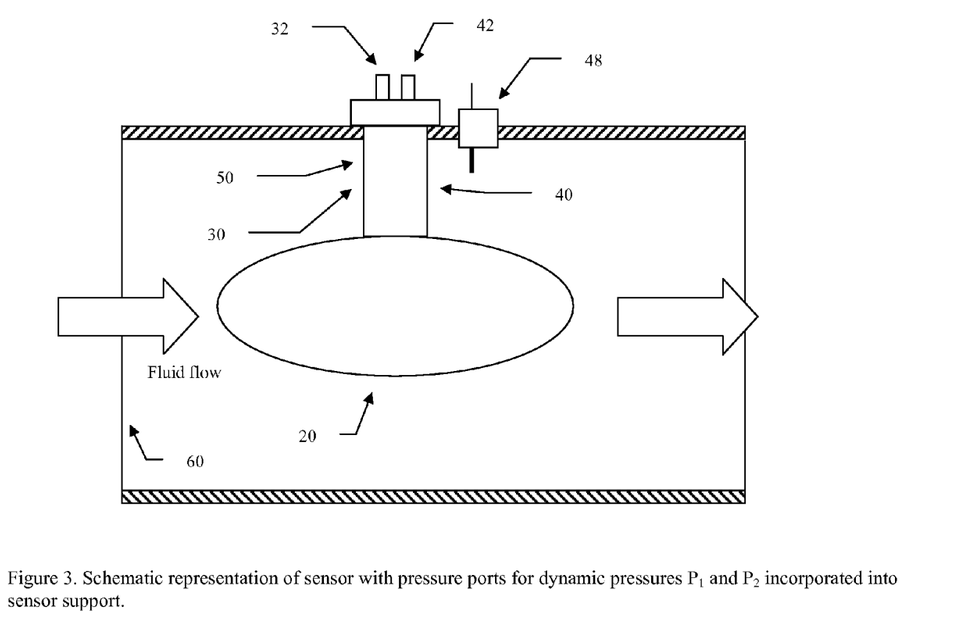
FIG. 3. Schematic representation of sensor with pressure ports for dynamic pressures $P_1$ and $P_2$ incorporated into sensor support.

FIG. 3 illustrates yet another embodiment, wherein support structure 50 includes built-in dynamic pressure sensing ports 30 and 40 thereby eliminating the need for a separate support as illustrated by 15 in the previous embodiment (FIG. 1). However, the processing of the pressure and temperature signals and computation of mass flow rate, volumetric flow rate and density is identical to that of the previous embodiment (FIG. 1), which is schematically illustrated in FIG. 2.

Figure 4:
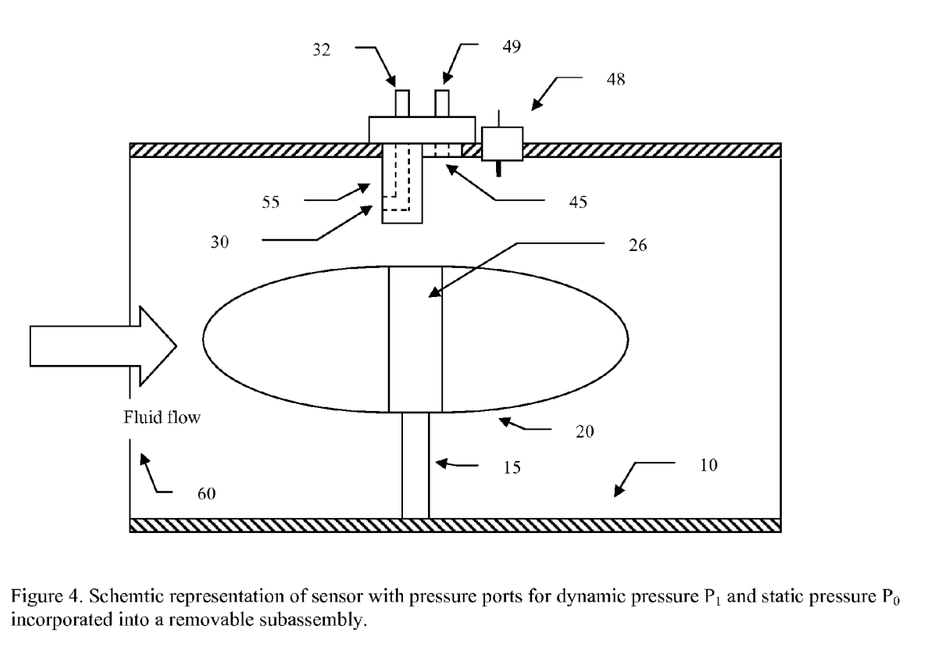
FIG. 4. Schematic representation of sensor with pressure ports for dynamic pressure and static pressure incorporated into a removable insert.

In yet another embodiment, with reference to FIG. 4, only one dynamic pressure signal (from pressure port 30) is obtained which reduces the resulting dynamic pressure signal by a factor of about one-half compared to embodiments illustrated in FIG. 1 or 3.

The second pressure signal obtained is that of fluid static pressure sensed internally at port 45 which is substantially flush with the inner wall of the cylindrical housing and, as such, is responsive to only hydrostatic pressure, but not fluid dynamic pressure. Signal processing in this embodiment is similar to previous embodiments. When fluid is flowing, only the upstream dynamic pressure $P_1$ measured at 30 and is expressed as $$P_1=\tfrac{1}{2}\rho V^2+P_0 \quad (32)$$

The static pressure of the fluid, $P_0$, is measured from external port 49 (FIG. 4).

Note that if $P_0$ is subtracted from $P_1$ one obtains $$P_1-P_0=\rho V^2 \quad (33)$$

$$P_0=ZRT\rho \text{ (gases)} \quad (34)$$

For gases, if (33) is divided by (34) one obtains $$(P_1-P_0)/P_0=V^2/ZRT \text{ (gases)} \quad (35)$$

Thus, the average fluid velocity V in the annular region can be expressed as $$V=\{ZRT(P_1-P_0)/P_0\}^{1/2} \text{ (gases)} \quad (36)$$

For gases, the volumetric flow rate $Q_{VG}$ can be expressed from (6) above as $$Q_{VG}=AV=A\{ZRT(P_1-P_0)/P_0\}^{1/2} \quad (37)$$

Using (7) above, the associated gas mass flow rate $Q_{MG}$ is given by $$Q_{MG}=\rho_G AV=A\{(P_1-P_0)P_0/ZRT\}^{1/2} \quad (38)$$

Gas density $\rho_G$ can be expressed as $$\rho_G=P_0/(ZRT) \quad (39)$$

Figure 5:
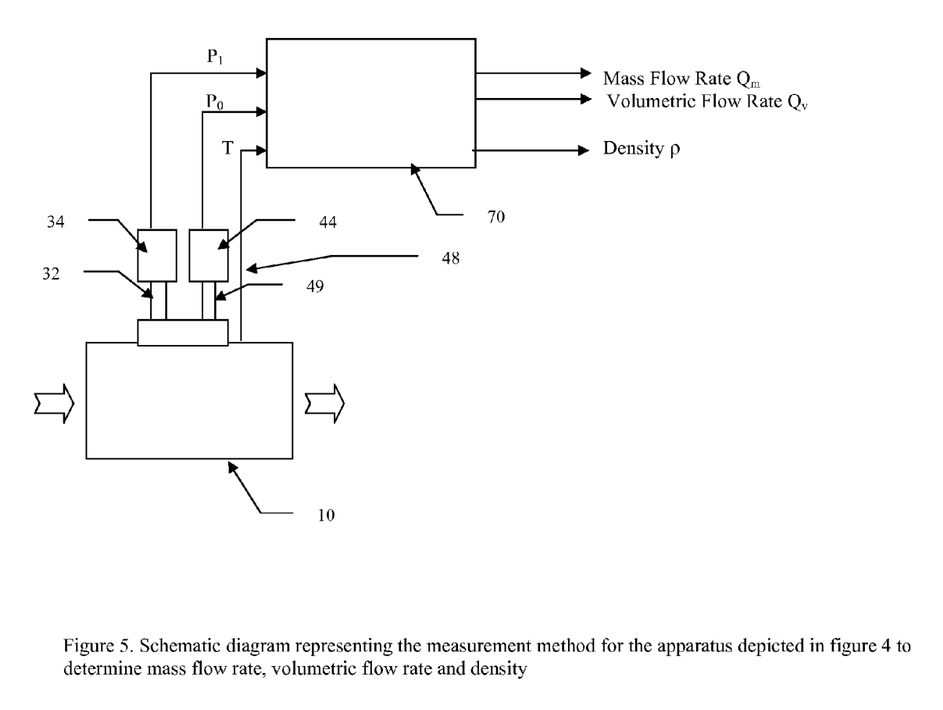
FIG. 5. Schematic diagram illustrating the measurement method and process for the embodiment depicted in FIG. 4.

Signal processing for this embodiment is schematically represented in FIG. 5.

It is understood that other pressure sensing arrangements can be applied to the present invention without departing from the teaching of the present invention. For example, differential pressure sensing means could also be employed to measure $P_1-P_2$ directly using two pressure sensing ports like 32 and 42, but without measuring either pressure individually in which case a third static pressure sensing port would also be required to measure static pressure $P_0$ akin to 45 in FIG. 4. Alternatively, dynamic pressure measurements $P_1$ and $P_2$ (or $P_0$) could also be performed with each pressure sensing measurement obtained at a different physical location along the length and/or circumference of the annular region.

The average fluid velocity is higher in the annular region resulting from that region's smaller area compared to that at the entrance to the flow sensor. Increased fluid velocity increases dynamic pressure quadratically thereby producing larger dynamic pressure signal levels. For example, doubling the fluid velocity quadruples the signal. Thus, measuring dynamic pressure in this region of comparatively higher fluid velocity enhances measurement sensitivity and the ability to measure increasingly lower flow rates.

FIG. 4 further emphasizes the distinctions between the present invention and that described in the '957 patent. In the present invention, only one dynamic pressure measurement is required which is responsive to the fluid's kinetic energy in the annular region, whereas the '957 patent requires two dynamic pressure sensors that measure across the flow-body structure of the '957 patent.

In the present invention, the elongated cylindrical structure alters the fluid flow as it is channeled into and through the annular region. Thus, upstream flow disturbances that could otherwise perturb a dynamic pressure measurement if performed at the tip of the cylindrical structure and adversely influence flow measurement accuracy are avoided in the present invention. Larger dynamic pressure signal levels at the point of measurement and reduced immunity to upstream flow disturbances are significant benefits of performing dynamic pressure measurements within in the annular region in addition to providing the mirror-image symmetrical pressure sensing arrangement discussed in the following paragraph.

With reference to FIGS. 1 and 3, if the streamline-shaped ends 22 and 24 have identical shape and if the upstream and downstream pressure sensing ports 30 and 40 are substantially centered about the lateral mid-point of the cylindrical structure thereby creating substantial structural symmetry, then the sensor has substantial symmetry with respect to measuring fluid flow in either flow direction. Accordingly, the flow sensor structure will present substantially equal impedance to fluid flow in either the "forward" or "reverse" direction thereby simplifying calibration and enhancing measurement accuracy for measuring bi-directional flows. These considerations are of particular importance for pulmonary applications where a sensor must present substantially equal impedance to air flow in both flow directions, otherwise unequal impedances to flow direction will skew the data complicating analysis of results.

Figure 6:
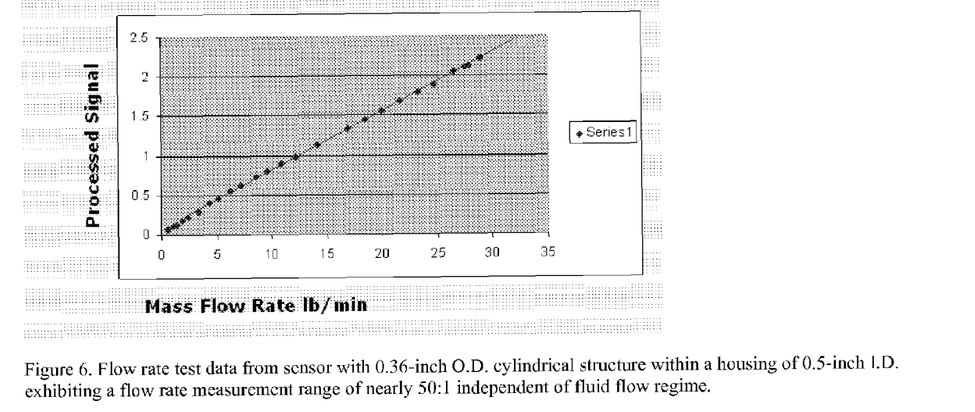
FIG. 6. Sensor with 0.36-inch O.D. cylindrical structure within a housing of 0.5-inch I.D. exhibits a flow rate measurement range on water of nearly 50:1 independent of fluid flow regime.

FIG. 6 illustrates flow rate test data on water obtained with a sensor similar in design to that schematically represented in FIG. 1. The sensor employs an elongated cylindrical structure of 0.36-inch O.D. and 0.75-inch length with "bullet"-shaped ends contained within a sensor housing of 0.5-inch I.D. The sensor exhibits an observed flow rate measurement range of 47:1. Significantly, the tests spanned flow rates with the flow regime varying from laminar (Re=464 at lowest flow rate) through the transition region and into the turbulent regime (Re=21,900 at maximum flow rate). The lack of any observed instability illustrates the sensor's response to flow rate is independent of flow regime in contrast to many other types of flowmeters (e.g., differential pressure, ultrasonic, turbine and vortex shedding).

Figure 7:
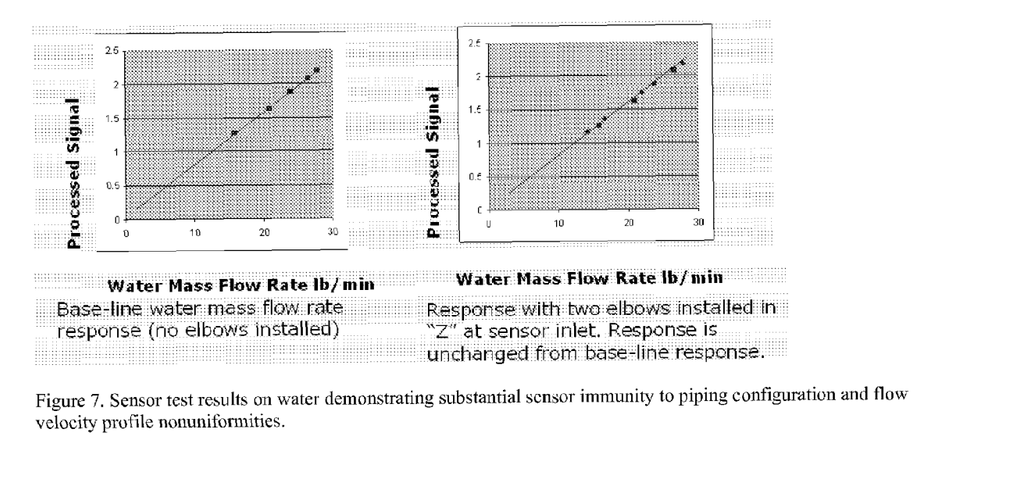
FIG. 7. Test results demonstrating sensor immunity to piping configuration and flow velocity profile non-uniformities.

FIG. 7 illustrates test data obtained using the same sensor as tested in FIG. 6 and illustrates the sensor's immunity to non-uniformities in flow velocity profile. The sensor's response was measured with water at several flow rates to establish a "base-line" response. Then two elbows were installed at the inlet to the sensor, which are known to introduce a skewed, non-uniform flow velocity profile across the inlet to the sensor. Yet the sensor's response observed with two elbows installed at the sensor inlet plotted together with the "base-line" data (i.e., no elbows) indicates no appreciable change in sensor response.

Consequently, the elongated cylindrical structure alters or transforms the fluid flow in such a way that, the resulting flow rate measurements (performed in the annular region) are substantially independent of flow regime and immune to variations and disturbances in flow velocity profile thereby offering a substantial improvement over conventional flow rate measurement devices.

Yet another embodiment of the present invention is based on applying the improved measurement method of the present invention to the apparatus described in the '957 patent.

The '957 patent teaches a mass flow measurement by subtracting two dynamic pressure measurements, which however differ substantially from those of the present invention.

As set forth in the Background of the Invention section, in FIG. 4 of the '957 patent, a first dynamic pressure measurement $P_1$ is obtained at the apex of a conically-shaped endpiece; a second dynamic pressure measurement $P_2$ is obtained at a different location from a pressure port located within the "cylindrical portion" of the body. According to the '957 patent, solely the difference between these two dynamic pressure signals determines fluid mass flow rate. In contrast to the present invention, the '957 patent teaches measuring a different dynamic pressure differential and teaches a different relationship between fluid mass flow and the measured pressure difference. The '957 patent teaches that the dynamic pressure difference measured across a "flow body" (from cone apex to "cylindrical portion") is sufficient to determine mass flow rate. In contrast to the '957 patent, the present invention employs two pressure measurements performed at substantially the same physical location within the annular region. Yet another important distinction between the '957 patent and the present invention is that the flow measurement described in the '957 patent is not density independent, which is a fundamental requirement for any fluid mass flow sensor. For example, FIG. 6 of the '957 patent illustrates that the response of the '957 flow sensor produces distinctly different responses to gases of different density (i.e., air and Argon). However, if the difference between the two pressure signals described in the '957 patent were sufficient to determine mass flow rate, then the responses would be the same for the two gases. By contrast, the mass flow measurement method of the present invention inherently accounts for fluid density. As a result, the teaching of the '957 patent that pressure differential alone determines mass flow rate differs from that of the present invention.

The '957 patent further states that "Dynamic pressure measurements, $P_1$ and $P_2$, result from the stable and smooth vortex trail generated by flow body 42" asserting that such pressure signals are produced by prominent "vortex generated differential pressures". By contrast, the operation of the present invention involves no vortices, but rather relies solely on measuring the dynamic pressure resulting from the kinetic energy of the fluid flowing in the annular region where there is no vortex trail caused by the "flow body". Furthermore, because the elongated cylindrical structure of the present invention is necessarily of streamlined-shape, it cannot produce vortices.

However, despite these significant differences between the '957 patent and the present invention, a device such as that described in the '957 patent (e.g., FIGS. 4, 12, 16 or 19) could benefit from the improved flow measurement method described herein. In particular, the signal processing method schematically depicted in FIG. 2 of the present invention, which simultaneously determines fluid mass flow rate, volumetric flow rate and gas density, could be applied beneficially to the type of flow body device described in the '957 patent, though not with the same accuracy because the device in the '957 patent would exhibit a hydrostatic pressure drop between the two pressure sensing locations that varies with flow rate because of the cylindrical structure interposed between that invention's two pressure sensing locations. Such is not the case with the present invention.

In contrast with other flow measurement devices employing either a static or dynamic differential pressure measurement across a flow obstruction or a flow constriction (including that described in the '957 patent), the dynamic pressure measurements of the present invention are performed at substantially the same location but with opposite upstream-downstream orientation in one embodiment (e.g., FIGS. 1 and 3) and only one dynamic pressure measurement (e.g., FIG. 4) in another embodiment.

Unlike the flow body of the '957 patent, the elongated cylindrical structure of the present invention 20 has no channels or passageways that could clog or otherwise become contaminated (a requirement for sanitary service or medical applications) and accordingly is less expensive to fabricate.

An embodiment of the present invention (as schematically depicted in FIG. 1) uses a pressure sensor assembly 41 akin to that of a Pitot-tube allowing for straightforward assembly, removal and replacement for cleaning if required whereas the entire sensor of the '957 patent requires disconnection and removal from the attached conduit for cleaning.

The foregoing detailed description of the invention has been presented for purposes of illustration and description. It is not intended to be exhaustive or to limit the invention to the precise form disclosed. Many modifications and variations are possible in light of the above teaching. The described embodiments were chosen in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A system for measuring fluid flow through a conduit having a central axis, the device comprising:
    a first pressure responsive element for measuring dynamic and static pressure, the first pressure responsive element having a first opening at a radial position relative to the central axis, the first opening facing a direction opposite to a direction of fluid flow through the conduit;
    a second pressure responsive element for measuring one of dynamic and static pressure;
    the first and second pressure responsive elements allowing the determination of each of mass flow rate, volumetric flow rate and a density of the fluid; and
    a structure supported in a fixed position circumjacent about the central axis, the structure reducing a cross-sectional area of the conduit in the area of the structure.

2. A system as recited in claim 1, the second pressure responsive element capable of measuring static pressure and having an opening facing a direction substantially perpendicular to the direction of fluid flow through the conduit.

3. A system as recited in claim 1, the second pressure responsive element capable of measuring dynamic pressure and having an opening facing a direction substantially opposite to the direction of the first opening.

4. A system as recited in claim 1, the structure having first and second tapering sections and a cylindrical section between the first and second tapering sections, the tapering and cylindrical sections being concentric about the central axis.

5. A system as recited in claim 4, wherein a plane through a cross-section of the structure midway between the first and second sections and perpendicular to the direction of fluid flow defines first and second halves of the structure, the first half being the same shape as the second half.

6. A system for measuring fluid flow through a conduit having a central axis, the device comprising:
    a first port for measuring dynamic and static pressure, the first port having a first opening at a fixed radial position relative to the central axis, the first opening facing a direction opposite to a direction of fluid flow through the conduit;
    a second port for measuring static pressure, the second port having an opening facing a direction substantially perpendicular to the direction of fluid flow through the conduit;
    a structure supported in a fixed position circumjacent about the central axis, the structure reducing a cross-sectional area of the conduit in the area of the structure;
    a temperature sensor for sensing a temperature of the fluid; and
    a processor for determining at least one of a mass flow rate of the fluid, a volumetric flow rate of the fluid and a density of the fluid from the measurements taken by the first port, second port and temperature sensor.

7. A system as recited in claim 6, wherein the first opening of the first port is located at an radial position between an outer wall of the structure and a wall of the conduit.

8. A system as recited in claim 6, the structure having first and second tapering sections and a cylindrical section between the first and second tapering sections, the tapering and cylindrical sections being concentric about the central axis.

9. A system as recited in claim 6, wherein the first and second tapering sections have the same shape.

10. A system as recited in claim 6, wherein the first and second tapering sections have different shapes.

11. A system as recited in claim 6, wherein a plane through a cross-section of the structure midway between first and second ends of the structure and perpendicular to the direction of fluid flow defines first and second halves of the structure, the first half being the same shape as the second half.

12. A system as recited in claim 6, wherein a plane through a cross-section of the structure midway between the first and second ends and perpendicular to the direction of fluid flow defines first and second halves of the structure, the first half having a different shape than the second half.

13. A system as recited in claim 6, wherein the structure provides a substantially constant fluid flow velocity across a cross-sectional area of the conduit including the structure.

14. A system as recited in claim 6, the first port and the second port forming an integral subassembly removable from the conduit.

15. A system for measuring fluid flow through a conduit having a central axis, the device comprising:
    a first port for measuring dynamic and static pressure, the first port having a first opening at a fixed radial position relative to the central axis, the first opening facing a direction opposite to a direction of fluid flow through the conduit;
    a second port for measuring dynamic and static pressure, the second port having a second opening at the same radial position relative to the central axis as the first opening, the second opening facing the same direction as a direction of fluid flow through the conduit;
    a structure supported in a fixed position circumjacent about the central axis, the structure reducing a cross-sectional area of the conduit in the area of the structure;
    a temperature sensor for sensing a temperature of the fluid; and
    a processor for determining at least one of a mass flow rate of the fluid, a volumetric flow rate of the fluid and a density of the fluid from a difference in the measurements taken by the first and second ports, and the temperature sensor.

16. A system as recited in claim 15, wherein the first and second openings of the first and second ports are located at an radial position between an outer wall of the structure and a wall of the conduit.

17. A system as recited in claim 15, the structure having first and second tapering sections and a cylindrical section between the first and second tapering sections, the tapering and cylindrical sections being concentric about the central axis.

18. A system as recited in claim 15, wherein the first and second tapering sections have the same shape.

19. A system as recited in claim 15, wherein the first and second tapering sections have different shapes.

20. A system as recited in claim 15, wherein a plane through a cross-section of the structure midway between the first and second ends defines first and second halves of the structure, the first half being the same shape as the second half.

21. A system as recited in claim 15, wherein a plane through a cross-section of the structure midway between the first and second ends defines first and second halves of the structure, the first half having a different shape than the second half.

22. A system as recited in claim 15, the first port and the second port forming an integral subassembly removable from the conduit.

23. A method of measuring fluid flow through a conduit having a central axis, the method comprising the steps of:
    (a) decreasing a cross-sectional area across which fluid flows in a section of the conduit by positioning a structure within the conduit;
    (b) measuring a dynamic pressure with an inlet port having an opening in the section of conduit of decreased cross-sectional area, the opening facing upstream relative to a direction of the fluid flow;
    (c) measuring a static pressure with an inlet port having an opening perpendicular to the direction of fluid flow; and
    (d) determining the fluid flow of the fluid through the conduit based on the measurements taken in said steps (b) and (c).

24. A method as recited in claim 23, said step (b) of measuring a dynamic pressure with the inlet port having an opening comprising the step of measuring a dynamic pressure with the opening of the inlet port positioned between a wall of the structure and a wall of the conduit.

25. A method as recited in claim 23, said step (d) of determining the fluid flow of the fluid through the conduit comprising the step of measuring a temperature of the fluid moving through the conduit.

26. A method as recited in claim 23, said step (c) of determining the fluid flow of the fluid through the conduit comprising the step determining a mass flow rate of the fluid through the conduit.

27. A method as recited in claim 23, said step (c) of determining the fluid flow of the fluid through the conduit comprising the step determining a volumetric flow rate of the fluid through the conduit.

28. A method of measuring fluid flow through a conduit having a central axis, the method comprising the steps of:
    (a) decreasing a cross-sectional area across which fluid flows in a section of the conduit by positioning a structure within the conduit;
    (b) measuring a dynamic pressure with one and only one inlet port having an opening in the section of conduit of decreased cross-sectional area, the opening facing upstream relative to a direction of the fluid flow;
    (c) measuring a static pressure with an inlet port having an opening perpendicular to the direction of fluid flow; and
    (d) determining the fluid flow of the fluid through the conduit based on the measurements taken in said steps (b) and (c).

29. A method as recited in claim 28, said step (b) of measuring a dynamic pressure with the inlet port having an opening comprising the step of measuring a dynamic pressure with the opening of the inlet port positioned between a wall of the structure and a wall of the conduit.

30. A method of measuring fluid flow through a conduit having a central axis, the method comprising the steps of:
    (a) measuring a first dynamic pressure of the fluid with a first inlet port at a distance from the central axis and facing a first direction relative to the fluid flow;
    (b) measuring a second dynamic pressure of the fluid with a second inlet port at the same distance from the central axis and facing a second direction opposite the first direction;
    (c) determining the fluid flow of the fluid through the conduit based on the measurements taken in said steps (a) and (b); and
    (d) increasing a dynamic pressure of the fluid measured in said step (a) by positioning an obstruction in the conduit in the area where the first dynamic pressure is measured to decrease a cross-sectional area of the conduit in an area where the first dynamic pressure is measured.

31. A method as recited in claim 30, said step (a) of measuring a first dynamic pressure of the fluid at a distance from the central axis comprising the step of positioning an opening of a first pressure port facing toward the direction of the fluid flow.

32. A method as recited in claim 31, said step (b) of measuring a second dynamic pressure of the fluid at the same distance from the central axis comprising the step of positioning an opening of a second pressure port facing away from the direction of the fluid flow.

33. A method as recited in claim 30, said step (c) of determining the fluid flow of the fluid through the conduit comprising the step of measuring a temperature of the fluid moving through the conduit.

34. A method as recited in claim 32, said step (c) of determining the fluid flow of the fluid through the conduit comprising the step using a dynamic pressure difference between the dynamic pressures measured in steps (a) and (b) that is twice the dynamic pressure of the fluid flowing through the conduit.

35. A method as recited in claim 30, said step (c) of determining the fluid flow of the fluid through the conduit comprising the step determining a mass flow rate of the fluid through the conduit.

36. A method as recited in claim 30, said step (c) of determining the fluid flow of the fluid through the conduit comprising the step determining a volumetric flow rate of the fluid through the conduit.

37. A method as recited in claim 30, further comprising the step (e) of minimizing turbulent flow of the fluid measured in said step (a) by positioning an obstruction in the conduit in the area where the first dynamic pressure is measured.

* * * * *